(12) United States Patent
Iwabuchi et al.

(10) Patent No.: US 7,705,152 B2
(45) Date of Patent: Apr. 27, 2010

(54) ALCOHOL OXIDATION CATALYST AND ITS PREPARATION PROCESS

(75) Inventors: Yoshiharu Iwabuchi, Sendai (JP); Masatoshi Shibuya, Sendai (JP); Masaki Tomizawa, Sendai (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 56 days.

(21) Appl. No.: 11/943,836

(22) Filed: Nov. 21, 2007

(65) Prior Publication Data

US 2008/0221331 A1     Sep. 11, 2008

(51) Int. Cl.
*C07D 453/06*     (2006.01)
(52) U.S. Cl. ...................................... 546/137
(58) Field of Classification Search .................. 546/137
See application file for complete search history.

(56) References Cited

FOREIGN PATENT DOCUMENTS

FR     1346190     * 11/1963

OTHER PUBLICATIONS

Dempwolf et al., Macromolecular Symposia (2007), 259(Polymer Reaction Engineering—International Workshop, 2007), 416-420.*
Gaudel-Siri et al., ChemPhysChem (2006), 7(2), 430-438.*
Engel et al., Journal of the American Chemical Society (2001), 123(16), 3706-3715.*
V. A. Golubev, et al, "Some Reactions Of Free Iminoxyl Radicals With The Participation Of The Unpaired Election", Journals of the Academy of Science USSR, No. 11, Jun. 17, 1965, pp. 1898-1904.
Lidia De Luca, et al, "Trichloroiscyanuric/Tempo Oxidation of Alcohols Under Mild Conditions: A close Investigation", J. Org. Chem., vol. 68, 2003, pp. 4999-5001.
Ross A. Miller, et al, "Iodine as A Chemoselective Reoxidant of TEMP: Application to the Oxidation of Alcohols to Aldehydes and Ketones", Organic Letters, vol. 5, No. 3, 2003, pp. 285-287.
Masatoshi Shibuya, et al, "2-Azaadamantane *N*-Oxyl (Azado) and 1-Me-Azado: Highly Efficient Organocatalysts for Oxidation of Alcohols", J. Am. Chem. Soc., vol. 128, 2006, pp. 8412-8413.
G. D. Mendenhall, et al, "Reactions of Bicyclic Nitroxides Involving Reduction of the NO Group[1]", Journal of the American Chemical Society, vol. 95, No. 19, Sep. 19, 1973, pp. 6395-6400.
Paul S. Engel, et al, "Thermolysis of Free-Radical Initiators: *tert*-Butylazocumene and Its 1,3- and 1,4-Bisazo and 1,3,5- Trisazo Analogues", Journal of the American Chemical Society, vol. 123, 2001, pp. 3706-3715.
S. F. Nelson, et al, "Geometry Change Upon Electron Removal from a Tetraalkylhydrazine . X-ray Crystallographic Structures of 9,9'-Bis-9-azabicyclo[3.3.1]nonane and Its Radical Cation Hexafluorophosphate", Journal of the American Chemical Society, vol. 100, No. 25, Dec. 6, 1978, pp. 7876-7882.
Takefumi Momose, et al, "Bicyclo[3.3.1]nonanes as Synthetic Intermediates. Part 19. 1 Asymmetric cleavage of w-azabicyclo[3.*n*.1]alkan-3-ones at the "Fork Head"", Journal of the Chemical Society, Perkin Trans., 1, 1997, pp. 1307-1313.

* cited by examiner

*Primary Examiner*—D. Margaret Seaman
*Assistant Examiner*—Niloofar Rahmani
(74) *Attorney, Agent, or Firm*—Oblon, Spivak, McClelland, Maier & Neustadt, L.L.P.

(57) ABSTRACT

An alcohol oxidation catalyst which is an organic oxidation catalyst to oxidize an alcohol, which contains azabicyclo [3.3.1]nonane N-oxyl represented by the following formula (1) having an N-oxyl group incorporated in a bicycle[3.3.1] nonane skeleton:

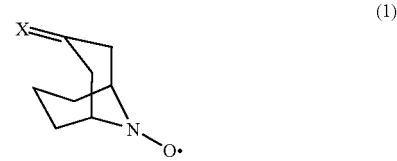

(1)

wherein X is $H_2$, O or NOH.

5 Claims, 2 Drawing Sheets 1-methyl-AZADO =

ABNO (9-azabicyclo[3.3.1]nonane N-oxyl)

ALCOHOL OXIDATION CATALYST AND ITS PREPARATION PROCESS

BACKGROUND OF THE INVENTION

1. Field of the Invention

The present invention relates to an organic oxidation catalyst to oxidize an alcohol, particularly an organic catalyst excellent in environmental harmonization and its preparation process. The present invention particularly relates to a technique to selectively oxidize an alcohol to an aldehyde, a ketone and/or a carboxylic acid, based on a nitroxyl radical.

2. Discussion of Background

Oxidation of an alcohol to a carbonyl compound is one of the most basic reactions in organic synthesis and heretofore, many excellent oxidizing agents and oxidation methods have been developed. Heretofore, oxidation reaction of an alcohol has been conducted by an oxidizing agent using a heavy metal such as a transition metal. However, a heavy metal such as a transition metal adversely affects the environment, and due to importance of the oxidation reaction of an alcohol, further increase in efficiency and improvement of the environmental harmonization are desired for the oxidation reaction of an alcohol.

In recent years, instead of a conventional oxidizing agent using a heavy metal, 2,2,6,6-tetramethylpiperidine N-oxyl (hereinafter sometimes referred to as "TEMPO") has been widely used as an oxidation catalyst for an alcohol since an experiment was disclosed in Non-Patent Document 1. The reaction mechanism is shown in FIG. 1. TEMPO is considered to be a low environmental burden type organic oxidation catalyst as compared with a heavy metal, and a combination of various bulk oxidizing agents with TEMPO, such as low environmental burden type NaOCl and $PhI(OAc)_2$, has been attempted as disclosed in Non-Patent Documents 2 and 3.

However, even TEMPO which has been widely used as an oxidation catalyst for an alcohol still has several problems. TEMPO is an excellent primary selective oxidation catalyst for a substrate in which a primary hydroxyl group and a secondary hydroxyl group coexist, but is not effective for oxidation of a secondary alcohol having a more sterically complicated structure and has limits to the catalytic activity. Further, TEMPO has a problem in stability in chemical structure such that decomposition is likely to occur as shown in FIG. 2 due to its chemical structure. Very recently, as an environmentally harmonizing oxidation catalyst which solves the above problems, 1-methyl-2-azaadamantane N-oxyl (hereinafter sometimes referred to as a "1-methyl-AZADO") which is another adamantane type nitroxyl radical as shown in FIG. 3 has been found by the present inventors. 1-Methyl-AZADO is an organic oxidation catalyst which applies a slight burden to environment like TEMPO, and which not only provides a higher catalytic turnover to a primary alcohol than TEMPO but also is capable of oxidizing a secondary alcohol having a sterically complicated structure, which is hardly oxidized by TEMPO, with high efficiency (Non-Patent Document 4).

As described above, 1-methyl-AZADO exhibits high catalytic activity not only to a primary alcohol but also to a secondary alcohol. However, its preparation is economically problematic since six steps are required from a commercially available compound, and use of expensive reagents is inevitable.

9-Azabicyclo[3.3.1]nonane N-oxyl (hereafter sometimes referred to as "ABNO") which is a bicyclo type nitroxyl radical highly structurally homologous to 1-methyl-AZADO having an adamantane skeleton, is a compound ranking as one of structural analogs of an azaadamantane type nitroxyl radical. Since it has been found to be present as a stable free radical like TEMPO, researches on its physical and chemical properties and researches on its application (e.g. a radical trapping agent, a radical generator, a spin labeling agent, etc.) as well have been conducted (Non-Patent Documents 5 and 6). However, its utilization as an alcohol oxidation catalyst has not been conducted at all.

ABNO is a known compound, but known preparation processes (including a process for preparing an amine-form as a precursor) have not been satisfactory from the viewpoint of mass supply (Non-Patent Documents 7 and 8).

Non-Patent Document 1: Golubev V. A. et. al: Izv. Akad. Nauk SSSR, Ser. Khim. 1965, p. 1927
Non-Patent Document 2: Lidia D. L., et al: J. Org. Chem. 2003, vol. 68, p, 4999
Non-Patent Document 3: Miller R. A., et al: Org. Lett. 2003, vol. 53, p 285
Non-Patent Document 4: Shibuya, M., et al: J. Am. Chem. Soc. 2006, vol. 128, p. 8412
Non-Patent Document 5: Mendenhall G. D., et al: J. Am. Chem. Soc. 1973, vol. 95, p. 6395
Non-Patent Document 6: Engel P. S., et al. J. Am. Chem. Soc. 2001, vol. 123, p. 3706
Non-Patent Document 7: Nelsen S. F., et al: J. Am. Chem. Soc. 1978, vol. 100, p. 7876
Non-Patent Document 8: Momose T., et al: J. Chem. Soc., Perkin Trans., 1, 1997, p. 1307

SUMMARY OF THE INVENTION

Development of an environmentally harmonizing organic oxidation catalyst has been required, having excellent properties comparable to 1-methyl-AZADO found to be an organic oxidation catalyst which applies a slight burden to environment like TEMPO, which provides a higher catalytic turnover to a primary alcohol than TEMPO, and which can oxidize a secondary alcohol having a sterically complicated structure, which is hardly oxidized by TEMPO, with high efficiency. Further, preparation of 1-methyl-AZADO is economically problematic since six steps are required from a commercially available compound and use of expensive reagents is inevitable. Thus, it is still desired that an environmentally harmonizing organic oxidation catalyst is easily provided at a low cost, with satisfactory mass supply.

The present inventors have conducted extensive studies to achieve the above object and as a result, noted 9-azabicyclo [3.3.1]nonane N-oxyl (ABNO) which is a bicyclo type nitroxyl radical highly structurally homologous to 1-methyl-AZADO having an adamantane skeleton, succeeded in finding its utilization as an oxidation catalyst, and accomplished the present invention.

The high alcohol oxidation catalytic activity of 1-methyl-AZADO is considered to be due to that its oxoammonium-form acquires a wide reaction field as compared with the existing TEMPO catalyst. Since ABNO is also a compound of which stability of the hydrogen atom at the α-position is secured due to the Bredt's rule, its bulkiness around the reaction site is reduced, and it is expected to fulfill functions at the same level as 1-methyl-AZADO as an alcohol oxidation catalyst. Further, the present inventors have conducted studies on a preparation process which makes mass supply of ABNO possible and as a result, they have succeeded in development of a synthetic route by which ABNO is prepared by three steps from inexpensive materials and which is excellent in workability and efficiency.

They have found that ABNO can be an organic oxidation catalyst capable of oxidizing a secondary alcohol having a sterically complicated structure which is hardly oxidized by TEMPO, with high efficiency like 1-methyl-AZADO, and in addition, providing the same or is higher catalytic turnover to a primary alcohol than TEMPO, and they have accomplished the present invention.

The present invention has been accomplished based on the above discoveries and further studies. Namely, the present invention provides the following.

(1) An alcohol oxidation catalyst which is an organic oxidation catalyst to oxidize an alcohol, which contains azabicyclo[3.3.1]nonane N-oxyl represented by the following formula (1):

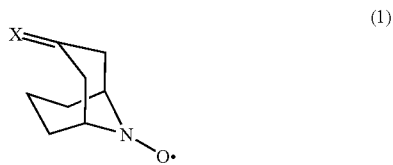

wherein X is $H_2$, O or NOH.

(2) A process for preparing an alcohol oxidation catalyst being an organic oxidation catalyst to oxidize an alcohol, which comprises subjecting acetonedicarboxylic acid, glutaraldehyde and ammonia water as basic materials to condensation reaction, hydrogenating the ketone moiety in the obtained bicyclo-form under Wolff-Kishner conditions, and oxidizing the amine moiety in the bicyclo-form.

(3) A process for preparing 9-azabicyclo[3.3.1]nonane N-oxyl, which comprises (a) subjecting acetonedicarboxylic acid, glutaraldehyde and ammonia water to condensation reaction to form 9-azabicyclo[3.3.1]nonane ring, (b) hydrogenating the ketone moiety in the obtained bicyclo-form under Wolff-Kishner conditions to form 9-azabicyclo[3.3.1]nonane, and (c) oxidizing the amino group in the obtained amine-form.

(4) A process for preparing 9-azabicyclo[3.3.1]nonane N-oxyl, which comprises (i) hydrogenating 9-azabicyclo[3.3.1]nonan-3-one under Wolff-Kishner conditions to produce 9-azabicyclo[3.3.1]nonane, and (ii) oxidizing the amino group in the obtained amine-form.

(5) A catalyst for preparation of an organic compound, which contains azabicyclo[3.3.1]nonane N-oxyl represented by the above formula (1).

(6) The catalyst according to the above (5), which is an oxidation catalyst for an organic compound.

(7) The catalyst according to the above (5) or (6), wherein the organic compound is an alcohol.

(8) A method of oxidizing an alcohol, which comprises oxidizing an alcohol in the presence of azabicyclo[3.3.1]nonane N-oxyl represented by the above formula (1) to prepare a corresponding oxo-form.

(9) An alcohol oxidation catalyst excellent in environmental harmonization, which is an organic oxidation catalyst to oxidize an alcohol, which contains 9-azabicyclo[3.3.1]nonane N-oxyl represented by the following formula (2) having an N-oxyl group incorporated in a bicyclo[3.3.1]nonane skeleton, and which has oxidation catalytic activity substantially at the same level as 1-methyl-AZADO:

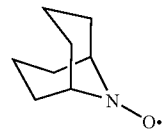

(10) A process for preparing an organic oxidation catalyst to oxidize an alcohol, excellent in workability, efficiency and economical efficiency, which comprises three steps of subjecting acetonedicarboxylic acid, glutaraldehyde and ammonia water which are available at a relatively low cost as raw materials to condensation reaction, hydrogenating the ketone moiety in the obtained bicyclo-form under Wolff-Kishner conditions, and oxidizing the amine moiety in the bicyclo-form, only with one purification operation.

(11) A process for preparing 9-azabicyclo[3.3.1]nonan-3-one, which comprises subjecting acetonedicarboxylic acid, glutaraldehyde and ammonia water to condensation reaction to form 9-azabicyclo[3.3.1]nonane ring.

The present invention further provides a technique to prepare an azabicycloalkane N-oxyl having a nitroxyl group incorporated in an azabicycloalkane skeleton, which is an organic oxidation catalyst to oxidize an alcohol, easily with high yield. In the present invention, an azabicycloalkane ring is formed by Mannich reaction and subsequent decarboxylation reaction. For example, acetonedicarboxylic acid, glutaraldehyde and ammonia water are subjected to condensation reaction to obtain a bicyclo-form such as 9-azabicyclo[3.3.1]nonan-3-one. Then, a ketone present in the formed bicyclo-form is reduced to obtain an amine-form. Then, the obtained amine is oxidized to obtain an N-oxyl form. Thus, the present invention provides a process for preparing a compound of the formula (1) to produce a large amount of an azabicycloalkane N-oxyl such as 9-azabicyclo[3.3.1]nonane N-oxyl, by three steps and one purification treatment step from raw materials easily available at a low cost with satisfactory yield by simple operation. The present invention provides a method of oxidizing an organic compound, using the organic compound of the above formula (1) as an organic oxidation catalyst, and a method of oxidizing an organic compound using, as an oxidizing agent, an oxoammonium salt prepared from the compound of the above formula (1) and chlorine.

The present invention provides a technique to oxidize an organic compound using, as an oxidizing catalyst, ABNO which can be produced easily in a large amount from inexpensive raw materials. The present invention provides a process for preparing ABNO by three steps from inexpensive raw materials. ABNO can be an organic oxidation catalyst not only capable of oxidizing a secondary alcohol having a spherically complicated structure which is hardly oxidized by TEMPO, but also providing the same or higher catalytic turnover to a primary alcohol than TEMPO, like 1-methyl-AZADO. In addition, its preparation process is easy and costs low as compared with 1-methyl-AZADO. According to the present invention, a catalyst to carry out alcohol oxidation reaction essential for production of organic functional materials such as pharmaceuticals, perfume and liquid crystal, effectively with low environmental burden, can be supplied in a large amount at a low cost, and the present invention is significantly effective industrially.

The other objects, characteristics, excellence and viewpoint of the present invention are obvious to those skilled in the art from the following description. However, it should be understood that the following description of the present specification including specific examples are only to describe the preferred embodiments. It is apparent to those skilled in the art that various changes and modifications are possible without departing from the concept and the scope of the present invention. All documents cited in the present specification are cited to describe the present invention, and the disclosures thereof are incorporated herein by reference.

DETAILED DESCRIPTION OF THE PREFERRED EMBODIMENTS

The present invention provides a technique to prepare an azabicyclo[3.3.1]nonane N-oxyl compound represented by the above formula (1) (such as azabicyclo[3.3.1]nonane N-oxyl represented by the above formula (2)) useful as a catalyst for preparation of an organic compound, particularly as an organic catalyst and oxidation catalyst, or its derivative (including a synthetic intermediate), and a technique to utilize such a compound.

Figure 1:
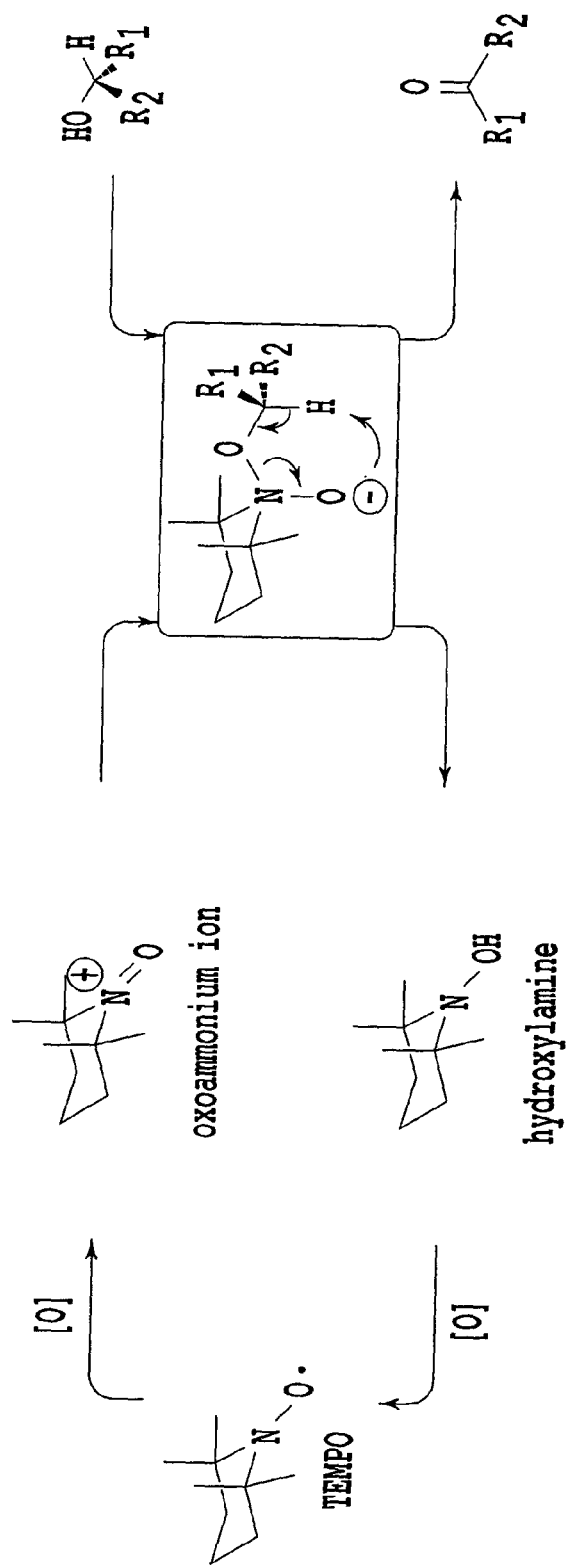
FIG. 1 is a view illustrating the reaction mechanism of TEMPO which is a conventional alcohol oxidation catalyst.
Figure 2:
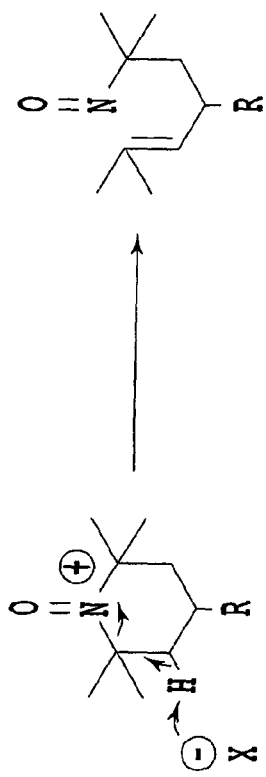
FIG. 2 is a view illustrating decomposition of TEMPO.
Figure 3:
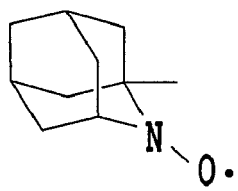
FIG. 3 is a view illustrating the structural formula of 1-methyl-AZADO.
Figure 4:
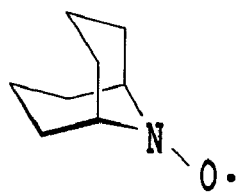
FIG. 4 is a view illustrating the structural formula of ABNO.

Now, the present invention will be described in detail with reference to 9-azabicyclo[3.3.1]nonane N-oxyl (ABNO, see FIG. 4) as a representative example of the azabicyclo[3.3.1] nonane N-oxyl compound represented by the above formula (1) or its derivative. However, it is apparent to those skilled in the art that the same applies to the other compounds.

ABNO which is an organic oxidation catalyst of the present invention is an azabicyclo[3.3.1]nonane N-oxyl type compound having an N-oxyl group incorporated in a bicyclo [3.3.1]nonane skeleton. An oxoammonium ion is a chemical species which quickly oxidizes an alcohol to a corresponding aldehyde or ketone under moderate conditions. ABNO which is an organic oxidation catalyst of the present invention stably forms such an oxoammonium ion on the bicyclo[3.3.1] nonane skeleton in the same manner as 1-methyl-AZADO.

ABNO has a structure represented by the following formula (2):

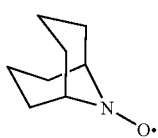
(2)

By incorporating an N-oxyl group in the bicyclo[3.3.1] nonane skeleton, hydrogen at the α-position is stabilized by the Bredt's rule, stability of the N-oxyl group is secured, the steric hindrance reduces as compared with TEMPO, and a wide reaction field is secured. Accordingly, ABNO can oxidize a secondary alcohol having a sterically complicated structure which is hardly oxidized by TEMPO, with high efficiency like 1-methyl-AZADO. Further, this compound is highly stable in chemical structure like 1-methyl-AZADO, and can remarkably reduce possibility of decomposition as in TEMPO.

Further, its preparation process is easy and costs low as compared with 1-methyl-AZADO.

Now, a preferred process for preparing ABNO will be described.

In the preparation process of the present invention, an aimed azabicyclo[3.3.1]nonane N-oxyl compound can be obtained by carrying out three steps i.e. a first step of subjecting preferably compounds available at a relatively low cost, i.e. acetonedicarboxylic acid (3) (another name: α-ketoglutaric acid), glutaraldehyde (4) and ammonia water as basic materials to condensation reaction to form an azabicyclo [3.3.1]nonane skeleton, a second step of reducing the ketone present in the obtained bicyclo-form to form azabicyclo [3.3.1]nonane, and a third step of oxidizing the amino group in the amine-form, with only one purification operation required.

According to the preferred embodiment of the present invention, 9-azabicyclo[3.3.1]nonane N-oxyl can be obtained by three steps i.e. a step of subjecting acetonedicarboxylic acid (3), glutaraldehyde (4) and ammonia water as basic materials to condensation reaction, a step of hydrogenating the ketone moiety in the obtained bicyclo-form (5) under Wolff-Kishner conditions and a step of oxidizing the amino group in the amine-form (6) with only one purification operation required. These steps are shown in the following reaction scheme:

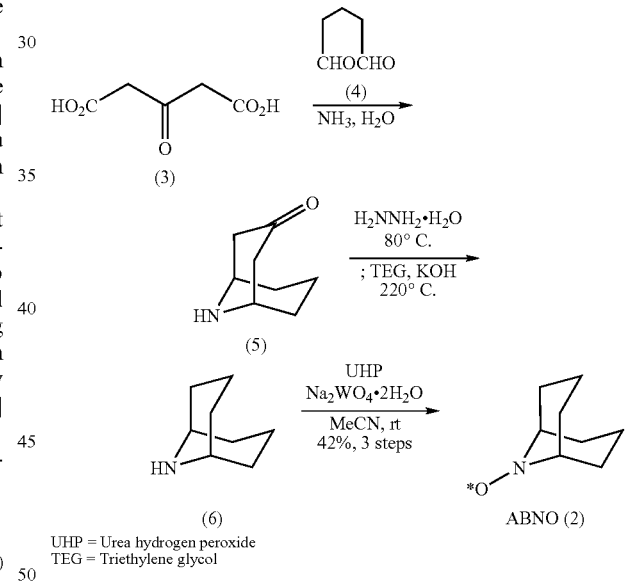

UHP = Urea hydrogen peroxide
TEG = Triethylene glycol

In the first step of the present invention, to an aqueous solution of acetonedicarboxylic acid (3) as a basic material, ammonia water and an aqueous solution of glutaraldehyde (4) are sequentially added slowly under cooling with ice to form a bicyclo-form (5) by condensation reaction. By condensation by Mannich reaction and subsequent decarboxylation, formation of 9-azabicyclo[3.3.1]nonane ring occurs to form 9-azabicyclo[3.3.1]nonan-3-one (5), which can be obtained as a powder only by removing excessive water and ammonia by a freeze-dryer after completion of the reaction.

In the second step of the present invention, the above bicyclo-form (5) and hydrazine (e.g. hydrazine hydrate ($H_2NNH_2 \cdot H_2O$)) are reacted to convert the ketone moiety to hydrazone, which is further reacted with a base such as KOH in a triethylene glycol solvent with heating (e.g. at 220° C.) for hydrogenation. Hydrogenation of the ketone moiety is carried out by Wolff-Kishner reaction to reduce a carboxyl group to a methylene group by hydrazine in the presence of a base such as sodium hydroxide or potassium hydroxide. The Wolff-Kishner reaction is carried out under basic conditions, and semicarbazide or an azide may be used instead of hydrazine. A modified Wolff-Kishner reaction may, for example, be a method of using tosylhydrazine and sodium cyanoborohydride, or a method of using bis TBS hydrazine for formation of hydrazone or treating hydrazone with potassium tert-butoxide ($^t$BuOK) in a DMSO-$^t$BuOH solvent at room temperature. For the Wolff-Kishner reaction, for example, documents such as Todd, D., Org. React., 4: 378 (1948) and Hutchins, R. O. & Hutchins, M. K., Comprehensive Organic Synthesis, 8: 327 (1991) may be referred.

In the second step of the present invention, water is added to the reaction product solution, and then using a simple distillation apparatus, a product of an amine-form can be obtained as an azeotropic mixture with water from the solution.

In the third step of the present invention, to an organic solvent solution (e.g. a MeCN solution) of the obtained amine-form (6), oxidizing agents such as urea hydrogen peroxide and $Na_2WO_4 \cdot 2H_2O$ are added under cooling with ice to oxidize the amino group. Oxidation is carried out usually at room temperature by stirring for a predetermined time (e.g. from 30 minutes to 24 hours, preferably from 2 to 8 hours) until completion of the reaction.

In the third step of the present invention, water is added to the reaction product solution, followed by extraction with an organic solvent such as chloroform or by purification and isolation by column chromatography to obtain aimed ABNO.

The reaction of oxidizing 9-azabicyclo[3.3.1]nonane represented by the above formula (6) or its derivative to obtain bicyclo[3.3.1]nonane N-oxyl represented by the above formula (1) or its derivative can be carried out by the above method under the above conditions or by a means under conditions disclosed in the present specification. For example, it can be carried out by bringing 9-azabicyclo[3.3.1]nonane or its derivative into contact with an oxidizing agent such as $Na_2WO_4 \cdot 2H_2O$, $H_2O_2$, NaOCl or an organic co-oxidizing agent, or a co-oxidizing agent as disclosed in Lidia D. L., et al: J. Org. Chem., vol. 68, p, 4999 (2003) or Miller R. A., et al: Org. Lett. vol. 53, p 285 (2003) in a proper solvent such as an anhydrous or hydrated alcohol solvent such as methanol, ethanol, propanol or isopropanol, an organic nitrile such as acetonitrile or an ether such as dioxane or tetrahydrofuran (THF). The oxidation may be carried out also by bubbling oxygen or gas containing active hydrogen such as ozone into the reaction mixture.

By sequentially carrying out the above steps, ABNO to be an organic oxidation catalyst excellent in environmental harmony can be prepared at a low cost by simple operation.

The compound disclosed in the present invention includes a free form, its salt (including an acid addition salt), its hydrate and its solvate, and any derivative derived from the functional group present in the molecule of the compound. The acid addition salt may be a salt with an acid selected from a halogen-containing inorganic proton acid, a phosphorus-containing inorganic acid, a sulfur-containing inorganic acid, a $C_{1-4}$ alkylcarboxylic acid, a perfluoro $C_{1-4}$ alkylcarboxylic acid and an aromatic carboxylic acid. Such an acid may, for example, be HCl, $HClO_4$, HBr, $HPF_6$, $H_3PO_4$, $H_2SO_4$, $CF_3COOH$, $CH_3COOH$, HCOOH or benzoic acid. The compound disclosed in the present invention may be properly isolated and purified as the case requires by known separation and purification means such as concentration, vacuum concentration, solvent extraction, crystallization, recrystallization, transfer to another solvent or chromatography.

Azabicyclo[3.3.1]nonane N-oxyl of the above formula (1) such as ABNO which is an organic nitroxyl radical of the present invention can convert a primary or secondary alcohol to a corresponding carbonyl compound such as an aldehyde, a ketone or a carboxylic acid by using an aqueous sodium hypochlorite solution, by use of its catalytic amount.

The catalyst for preparation of an organic compound of the present invention is characterized by containing azabicyclo[3.3.1]nonane N-oxyl represented by the above formula (1) in an effective amount as a catalyst. For use as a catalyst, the compound (1) may be added to a mixture containing reaction raw materials, or reaction raw materials may be added to a solvent containing the compound of the formula (1). The reaction may be two-phase system. The ratio of use of the compound of the formula (1) to the raw material organic compounds is not particularly limited so long as predetermined catalytic activity is obtained, and it is, for example, from 1/100,000 to 1/1, preferably from 1/10,000 to 2/3, more preferably from 1/1,000 to 1/10 by the molar ratio. The present catalyst may be added in a state of a mixture of the compound of the formula (1) with an oxidizing agent such as an aqueous sodium hypochlorite solution, to the reaction mixture. The catalyst is typically useful for oxidation reaction of an organic compound, for example, it can be used to oxidize an organic compound containing a group susceptible to oxidation reaction. The group susceptible to oxidation reaction may, for example, be a —OH group or a =O group. The organic compound may be a compound having a hydroxyl group, a carbonyl group or the like, and can be properly selected from organic compounds found by a search using database of Chemical Abstracts. Representative organic compounds include alcohols, thiols, aldehydes, ketones, carboxylic acids and their datives (including acid halides and esters), antibiotics, hydrocarbons, and polysaccharides such as cellulose.

The alcohol may, for example, be a primary alcohol or a secondary alcohol of the formula A-$CH_2$—OH or A-CH(OH)—B. Such an alcohol can be converted to a corresponding carbonyl compound in the presence of the present catalyst, for example, by using an oxidizing agent such as an aqueous sodium hypochlorite solution. As the oxidizing agent, an oxidizing agent which can be used for oxidation of the compound of the above formula (6) or its derivative can be used. The oxidizing agent can be properly selected depending upon the compound to be oxidized, and can be selected from ones known to be utilized for oxidation reaction using TEMPO. Such an oxidizing agent may, for example, be an oxygen-containing organic or inorganic compound. Typically, a peracid such as peracetic acid, hydrogen peroxide ($H_2O_2$), a hypohalite, a halite, a halide, a diacetoxyiodo allene, oxygen itself, or a combination thereof. The hypohalite is preferably an alkali metal hypohalite, an alkaline earth metal hypohalite or the like, and its may, for example, be LiOCl, NaOCl, KOCl, LiOBr, NaOBr or KOBr. Specifically, the oxidizing agent includes NaOCl, $PhI(OAc)_2$, NaOCl and NaBr, CaOCl, the air, oxygen, ozone, hypochlorous acid or its salt and $H_2O_2$, NaCl and NaOCl, chlorine dioxide ($ClO_2$), $ClO_2$ and $H_2O_2$, and the like.

In the primary or secondary alcohol of the formula A-$CH_2$—OH or A-CH(OH)—B, each of the groups A and B is not particularly limited so long as it is an organic group which has no adverse effect on the reaction, and it may, for example, be an alkyl group which may be substituted, a cycloalkyl group which may be substituted, an aromatic allotrope or heterocyclic ring which may be substituted. In the "alkyl group which may be substituted" represented by the above group A or B, the alkyl group may, for example, be a $C_{1-6}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl or 3,3-dimethylpropyl. The substituent of the alkyl group may, for example, be a lower alkoxy group (e.g. a $C_{1-6}$ alkoxy such as methoxy, ethoxy or propoxy), a halogen atom (such as fluorine, chlorine, bromine or iodine), a lower alkyl group (e.g. a $C_{1-6}$ alkyl such as methyl, ethyl or propyl), a lower alkenyl group (e.g. a $C_{2-6}$ alkenyl such as vinyl or allyl), a lower alkynyl group (e.g. a $C_{2-6}$ alkynyl such as ethynyl or propargyl), an amino group which may be substituted, a hydroxyl group which may be substituted, a sulfonyl group which may be substituted, a sulfonylamino group which may be substituted, a cyano group, a nitro group, a nitroso group, an amidino group which may be substituted, a carboxyl group, a lower alkoxycarbonyl group (e.g. a $C_{1-6}$ alkoxycarbonyl such as methoxycarbonyl or ethoxycarbonyl), a carbamoyl group which may be substituted (e.g. a carbamoyl group which may be substituted by a $C_{1-6}$ alkyl group which may be substituted by a 5- or 6-membered monocyclic aromatic hydrocarbon ring (e.g. pyridinyl) or an acyl group (e.g. formyl, a $C_{2-6}$ alkanoyl, benzoyl, a $C_{1-6}$ alkoxycarbonyl which may be halogenated, a $C_{1-6}$ alkylsulfonyl which may be halogenated, or benzenesulfonyl), 1-azetidinyl carbonyl, 1-pyrrolidinylcarbonyl, piperidinylcarbonyl, morpholinocarbonyl or 1-piperazinylcarbonyl), an alkyl group substituted by the following "cycloalkyl group which may be substituted" or "an aromatic allotrope or heterocyclic ring which may be substituted", an alkenyl group substituted by the following "cycloalkyl group which may be substituted" or "an aromatic allotrope or heterocyclic ring which may be substituted", an alkoxy group substituted by the following "cycloalkyl group which may be substituted" or "an aromatic allotrope or heterocyclic ring which may be substituted", a hydroxyl group substituted by the following "cycloalkyl group which may be substituted" or "an aromatic allotrope or heterocyclic ring which may be substituted", an amino group substituted by the following "cycloalkyl group which may be substituted" or "an aromatic allotrope or heterocyclic ring which may be substituted", or an acyl group substituted by the following "cycloalkyl group which may be substituted" or "an aromatic allotrope or heterocyclic ring which may be substituted". The alkyl group may be substituted by one to three such optional substituents at the substitutable position(s).

In the "cycloalkyl group which may be substituted" represented by the group A or B, the cycloalkyl group may, for example, be a $C_{3-7}$ cycloalkyl such as cyclopropyl, cyclobutyl, cyclopentyl, cyclohexyl or cycloheptyl. The substituent of the cycloalkyl group may be the same substituent as mentioned for the above "alkyl group which may be substituted", and the cycloalkyl group may be substituted by one to three substituents.

In the "aromatic allotrope or heterocyclic ring which may be substituted" represented by the group A or B, the aromatic allotrope or heterocyclic ring may, for example, be a monocyclic or condensed polycyclic aromatic carbocyclic ring, or a monocyclic or condensed polycyclic aromatic heterocyclic ring. It is preferably a $C_{6-14}$ aromatic carbocyclic ring (an aryl group) or a 5- to 14-membered aromatic heterocyclic ring (a heteroaryl group), more preferably a $C_{6-10}$ aromatic carbocyclic ring (aryl group) or a 5- to 10 membered aromatic heterocyclic ring (heteroaryl group), more preferably a $C_6$ aromatic carbocyclic ring (aryl group) or a 5- or 6-membered aromatic heterocyclic ring (heteroaryl group). Specifically, the "aromatic allotrope" may, for example, be pentazole; or a $C_{6-14}$ aryl group such as phenyl, naphthyl, anthryl, azulenyl, phenanthryl or acenaphthylenyl, particularly preferably phenyl, 1-naphthyl, 2-naphthyl or the like. The "aromatic heterocyclic ring" may, for example, be an aromatic heterocyclic ring containing, as an atom (annular atom) constituting the ring, at least one (preferably 1 to 4, more preferably 1 or 2) of one to three types (preferably one or two types) of hetero atoms selected from an oxygen atom, a sulfur atom, a nitrogen atom and the like.

Specifically, the "aromatic heterocyclic ring" may, for example, be a 5- or 6-membered monocyclic aromatic heterocyclic ring such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl or triazinyl, or a 8- to 12-membered condensed polycyclic aromatic heterocyclic ring such as benzofuranyl, isobenzofuranyl, benzo(b)thienyl, indolyl, isoindolyl, 1H-indazolyl, benzoindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxadinyl, phenothiadinyl, phenadinyl, phenoxathiinyl, thianthrenyl, phenanthridinyl, phenanthrolinyl, indolizinyl, pyrolo[1,2-b] pyridazinyl, pyrazolo[1,5-a]pyridyl, imidazo[1,2-a]pyridyl, imidazo[1,5-a]pyridyl, imidazo[1,2-b]pyridazinyl, imidazo [1,2-a]pyrimidinyl, 1,2,4-triazolo[4,3-a ]pyridyl or 1,2,4-triazolo[4,3-b]pyridazinyl. It is preferably a 5- or 6-membered monocyclic aromatic heterocyclic ring. The substituent in the "aromatic allotrope or heterocyclic ring which may be substituted" may be protected by a conventional method in organic synthesis as the case requires, it is not particularly limited so long as it has no influence over the reaction, and it may be known one in this field.

The primary or secondary alcohol may contain a hydrocarbon or a saccharide including cellulose. The saccharide may, for example, be a monosaccharide, a disaccharide, an oligosaccharide or a polysaccharide, which may be included in antibiotics, peptides or proteins. The primary or secondary alcohol may be a monomer, oligomer or polymer for preparation of pharmaceuticals including penicillin antibiotics, cephalosporin antibiotics, aminoglycoside antibiotics, macrolide antibiotics, tetracycline antibiotics, quinolone synthetic anti-fungus agents and antitumor agents, agricultural chemicals, colorants and polymers.

The present oxidation reaction may employ conditions known in this field. For example, it is carried out by adding an oxidizing agent to a solution containing reaction raw materials in the presence of an effective amount of the catalyst, or by adding an effective amount of the catalyst to a solution containing reaction raw materials and then adding an oxidizing agent. Oxidation reaction is carried out usually in a solvent, and the solvent may be properly selected from the above-described solvents. The type and the amount of the reaction raw materials, the amount of the catalyst, the type and the amount of the oxidizing agent, the type and the amount of the solvent, the reaction time, the reaction temperature and conditions for oxidation reaction such as stirring can be properly selected depending upon the specific object, and as the case requires, optimum conditions or more preferred conditions may be determined by experiments.

The above-described reaction may be carried out in the presence or absence of a solvent, and when it is carried out in the presence of a solvent, a conventional solvent which has no adverse effect on the reaction may be used. Such a solvent may, for example, be an aromatic hydrocarbon, an aliphatic hydrocarbon, an ether, an ester, an aliphatic halogenated hydrocarbon, an alcohol, an amide, an organic acid or water, and it is preferably, methanol, ethanol, propanol, isopropanol, n-butanol, ethyl acetate, butyl acetate, formic acid, acetic acid, hexamethylphosphoric amide, dimethylimidazolidinone, acetonitrile, N,N-dimethylformamide (DMF), dimethylacetamide, N-methylpyperidone, dimethyl sulfoxide (DMSO), pyridine, chloroform, 1,2-dichloroethane, dioxane, acetonitrile, toluene, benzene, xylene, hexane, pentane, heptane, tetrahydrofuran (THF), diethyl ether, diisopropyl ether, t-butyl methyl ether, 1,2-dimethoxyethane or methylene chloride. The solvent may be used alone or as a mixture of two or more of them, and it may be anhydrous or hydrated, and the solvent is properly selected. To the reaction system, a buffering agent may properly be added. The buffering agent may, for example, be a hydroxide of an alkali metal or an alkaline earth metal, a carbonate of an alkali metal or an alkaline earth metal, a bicarbonate of an alkali metal or an alkaline earth metal, or a phosphate of an alkali metal or an alkaline earth metal, and for example, sodium hydrogencarbonate, sodium acetate or a phosphate is preferably used.

The reaction temperature is from about −80 to about 200° C., preferably from about room temperature to about 150° C. The reaction time is selected so that the predetermined reaction is completed, and it is usually from about 1 hour to about 40 hours.

Now, the present invention will be described in further detail with reference to Examples. However, it should be understood that the present invention is by no means restricted to specific Examples. Obviously, various changes and modifications are possible within the intention and the scope of the present invention.

All examples were carried out or can be carried out by standard technique known to those skilled in the art, unless otherwise specified.

EXAMPLE 1

28% ammonia water (4.5 ml) was slowly added at 0° C. to an aqueous solution (50 ml) of acetonedicarboxylic acid (2.1 g, 14.4 mmol). At the same temperature, an aqueous solution (52.5 ml) of glutaraldehyde (1.44 g, 14.4 mmol) was added over a period of about 1 hour, followed by stirring at room temperature for 35 hours. After completion of the reaction was confirmed, the reaction solvent was removed to obtain a crude bicyclo-form.

Then, using the crude bicyclo-form as a raw material, the crude bicyclo-form (14.4 mmol) and $H_2NNH_2 \cdot H_2O$ (2.2 ml, 43.1 mmol) were reacted at 80° C. for 2 hours. Further, to a two-necked recovery flask equipped with a distillation apparatus, KOH (8 g, 144 mmol) and a triethylene glycol solution (21 ml) were added and heated at 220° C. The reaction solution containing the bicyclo-form was slowly added from a dropping funnel, followed by stirring at 220° C. for 30 minutes. At the same temperature, $H_2O$ (50 ml) was added dropwise over a period of 2 hours, and the product was separated from the reaction solution by azeotropic distillation. The obtained distilled component was subjected to extraction with chloroform, the obtained organic layer was dried over $K_2CO_3$, and the solvent was removed to obtain a crude amine-form.

Then, a MeCN solution (14.4 ml) of the crude amine-form, $Na_2WO_4 \cdot H_2O$ (0.95 g, 2.88 mmol) was added at room temperature, followed by stirring for 30 minutes. After cooling to 0° C., urea hydrogen peroxide (2.7 g, 28.8 mmol) was added, followed by stirring for 1 hour and then stirring at room temperature for 4 hours. After completion of the reaction was confirmed, $H_2O$ (50 ml) was added, followed by extraction with chloroform, and the obtained organic layer was dried over $K_2CO_3$. The solvent was removed, and the residue was subjected to column chromatography to obtain ABNO (0.84 g, 6 mmol). The present compound was subjected to mass spectrometry as electron ionized at an accelerating voltage of 3 kV under an ionizing voltage of 70 eV at an ionization current of 300 μA and as a result, a molecular ion peak at m/z 140 and a base peak (100%) at m/z 81 were obtained. Further, characteristic fragment ion peaks at m/z 67, 96, 107 and 122 were obtained.

Using ABNO prepared in such a manner, first, its activity as an oxidation catalyst to a primary alcohol as identified in Table 1 was examined. As the reaction conditions, using the catalyst in an amount as identified in Table 1, in $CH_2Cl_2$, 0.1 equivalent amount of KBr, 0.05 equivalent amount of n-$Bu_4NBr$ and 1.4 equivalent amounts of NaCl were further added, and the reaction was carried out under cooling with ice for 20 minutes. After completion of the reaction, the yield of the product was determined. The yield was calculated from (the amount of substance of the product)/(the amount of substance of the raw material)×100%. As Comparative Examples, the same reaction was carried out using TEMPO or 1-methyl-AZADO under the same reaction conditions to determine the yield. The obtained results are shown in Table 1.

TABLE 1

Ph~~~OH  →  nitroxyl radical / NaOCl (1.5 eq) / KBr (0.1 eq), n-Bu₄NBr (0.05 eq) / NaHCO₃ (aq.), CH₂Cl₂, 0° C., 20 min  →  Ph~~~O

| | | | yield (%) | |
|---|---|---|---|---|
| entry | eq | TEMPO | 1-methyl-AZADO | ABNO |
| 1 | 0.01 | 90 | 91 | 90 |
| 2 | 0.001 | 88 | 90 | 88 |
| 3 | 0.0001 | 23 | 91 | 85 |

ABNO of the present invention has, in a case where the catalyst amount was 0.01 equivalent amount, a function at the same level as conventional TEMPO and 1-methyl-AZADO as an oxidation catalyst for a primary alcohol and in addition, even when the amount of catalyst was reduced (0.0001 equivalent amount), a product with high yield could be obtained at the same level as a case of using conventional 1-methyl-AZADO (entries 1 to 3).

Then, using the prepared ABNO, its activity as an oxidation catalyst was examined in the same manner with respect to various secondary alcohols as identified in Table 2. As the reaction conditions, the amount of the catalyst was 0.01 equivalent amount, in $CH_2Cl_2$, 0.1 equivalent amount of KBr, 0.05 equivalent amount of n-$Bu_4NBr$ and 1.5 equivalent amount of NaOCl were further added, and the reaction was carried out under cooling with ice for 20 minutes. After completion of the reaction, the yield of the product was determined. The yield was calculated from (the amount of substance of the product)/(the amount of substance of the raw material)×100%. As Comparative Examples, the same reaction was carried out using TEMPO or 1-methyl-AZADO under the same reaction conditions to determined the yield. The obtained results are shown in Table 2.

TABLE 2 reaction scheme: R₁R₂CH(OH) → R₁R₂C(=O), conditions: nitroxylradical (0.01 eq), NaOCl (1.5 eq), KBr (0.1 eq), nBu₄NBr (0.05 eq), CH₂Cl₂, sat. NaHCO₃, 0° C., 20 min

| run | substrate | TEMPO | 1-Me-AZADO | ABNO |
|---|---|---|---|---|
| 1 | trans-2-phenylcyclohexanol | 16 | 99 | 99 |
| 2 | menthol | trace | 95 | 94 |
| 3 | Ph-CH(OH)-C(CH₃)₃ | 13 | 84 | 93 |
| 4 | 2,2-dimethyl-3-octanol | 15 | 93 | 95 |
| 5 | diacetone-type sugar with OH | 8 | 99 | 98 |
| 6 | 5′-O-TBS, 2′-O-TBS adenosine | 12 | 100 | 91 |

With respect to a secondary alcohol having a sterically bulky and complicated structure, the yield of an aimed product is low in a Comparative Example in which TEMPO is used, but by ABNO of the present invention, the secondary alcohol is quickly oxidized to form an aimed product with high yield at the same level as a case of using 1-methyl-AZADO.

Accordingly, it is apparent that ABNO has a function at substantially the same level as 1-methyl-AZADO and is a useful catalyst as an oxidation catalyst for not only a primary alcohol but also a secondary alcohol.

The catalyst of the present invention is an organic oxidation catalyst having an oxidation catalytic activity at the same level as an existing highly active alcohol oxidation catalyst 1-methyl-AZADO and is capable of being prepared by a process excellent in efficiency, workability and economical efficiency.

The organic oxidation catalyst can be obtained by three steps from inexpensive acetonedicarboxylic acid, glutaraldehyde and ammonia water as base materials with a total yield of 42%, and by the process of the present invention, ABNO having an N-oxyl group incorporated in a bicyclo[3.3.1] nonane skeleton can be supplied in a large amount with only one purification operation. Further, ABNO can be an organic oxidation catalyst capable of oxidizing a secondary alcohol having a sterically complicated structure which is hardly oxidized by TEMPO with high efficiency like 1-methyl-AZADO and further showing the same or high catalytic turnover to a primary alcohol than TEMPO.

The present invention provides an organic oxidation catalyst having an oxidation catalytic activity at the same level as the existing highly active alcohol oxidation catalyst 1-methyl-AZADO and capable of being prepared by a process excellent in efficiency, workability and economical efficiency. Such a catalyst is an organic oxidation catalyst for an alcohol excellent in environmental harmony and capable of effective oxidation. According to the present invention, an effective preparation process thereof is also available.

ABNO of the present invention is applicable to preparation of functional organic compounds, functional polymer materials and organic synthesis materials, represented by pharmaceuticals, agricultural chemicals, perfume, colorants and liquid crystal.

It is obvious that various changes and modifications are possible without departing from the concept and the scope of the present invention.

The entire disclosure of Japanese Patent Application No. 2007-055072 filed on Mar. 6, 2007 including specification, claims, drawings and summary is incorporated herein by reference in its entirety.

What is claimed is:

1. An alcohol oxidation catalyst comprising an oxidizing agent and azabicyclo[3.3.1]nonane N-oxyl represented by formula (1) having an N-oxyl group incorporated in a bicycle [3.3.1]nonane skeleton:

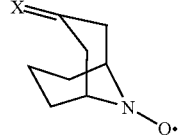

(1)

wherein X is $H_2$, O or NOH.

2. A process for preparing the alcohol oxidation catalyst according to claim 1, comprising:
   subjecting acetonedicarboxylic acid, glutaraldehyde and ammonia water to a condensation reaction to obtain a 9-azabicyclo[3.3.1]nonane ring,
   hydrogenating the ketone moiety in the obtained ring under Wolff-Kishner conditions, and
   oxidizing the amine moiety in the ring.

3. A process of oxidizing an alcohol comprising contacting the alcohol oxidation catalyst according to claim 1 with an alcohol.

4. The alcohol oxidation catalyst according to claim 1, wherein the oxidizing agent is sodium hypochlorite.

5. The process according to claim 3, wherein the alcohol is a primary or secondary alcohol.

* * * * *

UNITED STATES PATENT AND TRADEMARK OFFICE
CERTIFICATE OF CORRECTION

PATENT NO.       : 7,705,152 B2                                              Page 1 of 1
APPLICATION NO.  : 11/943836
DATED            : April 27, 2010
INVENTOR(S)      : Iwabuchi et al.

It is certified that error appears in the above-identified patent and that said Letters Patent is hereby corrected as shown below:

On the title page, Item (30), The Foreign Application Priority Data has been omitted. Item (30) should read:

-- (30)    Foreign Application Priority Data

Mar. 6, 2007    (JP) .................................. 2007-055072 --

Signed and Sealed this

Sixth Day of July, 2010

David J. Kappos
*Director of the United States Patent and Trademark Office*